US00PP36673P2

(12) United States Plant Patent
Grazzini

(10) Patent No.: US PP36,673 P2
(45) Date of Patent: May 13, 2025

(54) ***HIBISCUS* PLANT NAMED 'G21086'**

(50) Latin Name: *Hibiscus moscheutos*
Varietal Denomination: G21086

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 18/933,357

(22) Filed: Oct. 31, 2024

(51) Int. Cl.
*A01H 5/00* (2018.01)
*A01H 6/60* (2018.01)

(52) U.S. Cl.
USPC ..... Plt./257

(58) Field of Classification Search
USPC ..... Plt./226, 257
See application file for complete search history.

(56) References Cited

U.S. PATENT DOCUMENTS

PP32,036 P2 * 8/2020 Hansen ..... A01H 5/02
Plt./257

* cited by examiner

*Primary Examiner* — Karen M Redden
(74) *Attorney, Agent, or Firm* — Cassandra Bright

(57) ABSTRACT

A new and distinct cultivar of *Hibiscus moscheutos* plant named 'G21086' is disclosed, characterized by large cherry red flowers with a large red eye, and distinct venation radiating out from the central eye out into the petals. Eye color is only slightly darker than the color of flower petals. Flower size is large, about 6 to 7 inches. Emerging foliage is chocolate brown to violet. Plants are compact, growing to approximately 36 to 42 inches high and wide with dense basal branching. Plants emerge and flower earlier than is typical of the species. The new variety is a *Hibiscus moscheutos*, normally produced as an outdoor garden or container plant.

3 Drawing Sheets

Figure 1:
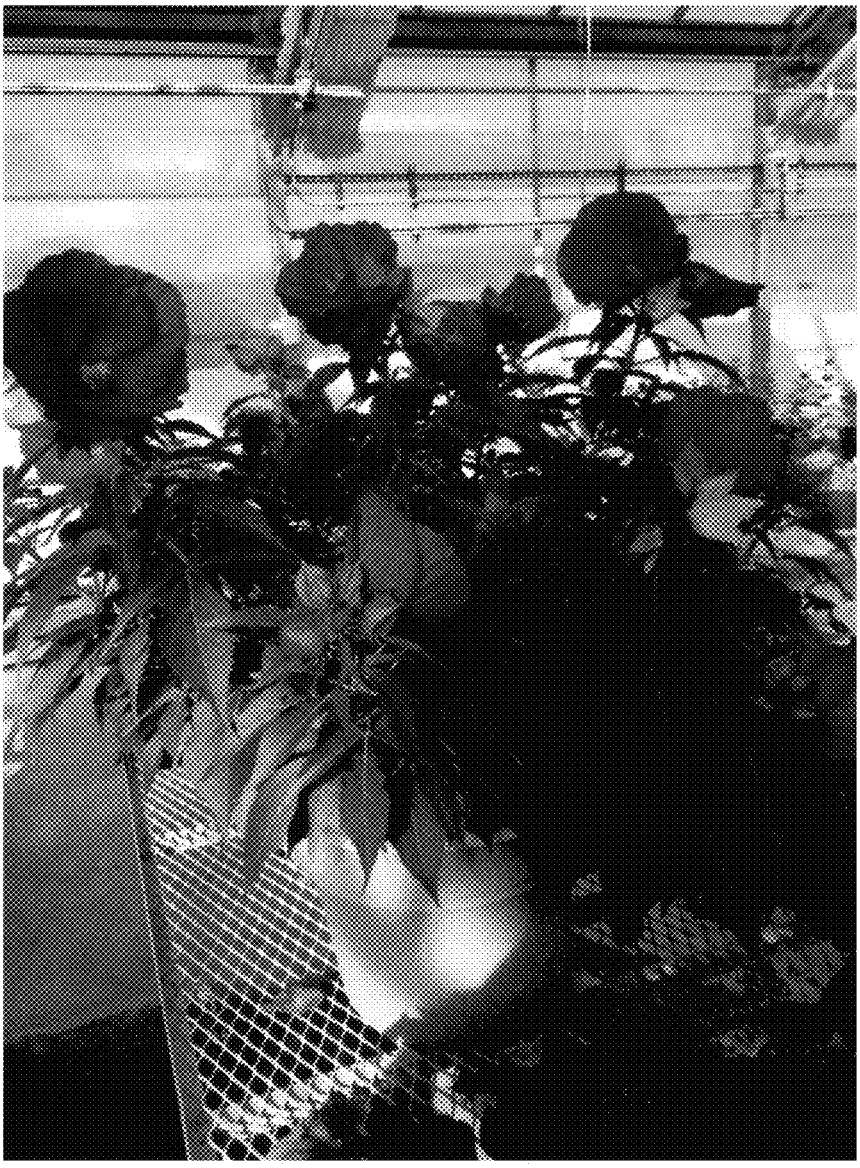

Latin name of the genus and species: *Hibiscus moscheutos*.

Vcultivar denomination: 'G21086'.

BACKGROUND OF THE INVENTION

The new cultivar is the product of a planned breeding program conducted by the inventor. The self-pollination resulting in the new cultivar was made between June 2016 and September 2017 at a research greenhouse in Bellefonte, Pennsylvania. The parent cultivar is an undistributed, unpatented proprietary cultivar referred to internally as 43450-3. The new cultivar 'G21086' was derived from self-pollinating 43450-3. Selection of 'G21086' was made at the same research greenhouse in Bellefonte, PA in August of 2019.

Asexual reproduction of the new cultivar 'G21086' by terminal vegetative cuttings was performed at the same nursery in Bellefonte, Pennsylvania in June of 2020. Subsequent asexual reproduction, including from tissue culture has shown that the unique features of this cultivar are stable and reproduced true to type through successive generations.

SUMMARY OF THE INVENTION

The cultivar 'G21086' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G21086'.

These characteristics in combination distinguish 'G21086' as a new and distinct *Hibiscus* cultivar:

1. 'G21086' has bright cherry-red flowers with a large red eye, and distinct venation radiating out from the central eye out into the petals. Eye color is only slightly darker than the color of flower petals.
2. 'G21086' has flowers of large size, typically 6" to 7" in diameter on a well-grown plant.
3. 'G21086' has chocolate-brown to dark violet leaves, with slightly pubescent non-glossy leaf surfaces above and below.
4. 'G21086' has a high number of shoots (5 to 8 or more) emerging from the base of the plant as it emerges from dormancy.
5. 'G21086' emerges from dormancy in the spring up to a month earlier than is typical for the species.
6. 'G21086' flowers up to a month earlier than is typical for the species.
7. 'G21086' has a compact, densely branched habit, reaching a size of 36" to 42" high and wide.
8. 'G21086' has been shown to be winter hardy to at least USDA zone 5.

PARENT COMPARISON

Plants of the new cultivar 'G21086' are similar to plants of the parent cultivar, in most horticultural characteristics. However, plants of the new cultivar 'G21086' differ in the following:

1. 'G21086' has cherry-red flowers and distinct dark venation in the flower petals. Parent 43450-3 has light red flowers, and minimal to no venation.

2. 'G21086' has chocolate-brown to dark violet leaves, with slightly pubescent non-glossy leaf surfaces above and below. 43450-3 has dark violet leaves and a glossy leaf surface.
3. 'G21086' has a high number of shoots (5 to 8 or more) emerging from the base of the plant as it emerges from dormancy. 43450-3 has a moderate number of shoots (3 to 5) as it emerges from dormancy.
4. Parent 43450-3 flowers a week to 10 days later than 'G21086'.
5. 'G21086' has a compact habit, reaching a size of 36" to 42" high and wide. 43450-3 is larger and more open in habit, reaching 40" to 48" in height and width.

COMMERCIAL COMPARISON

'G21086' can be compared to the commercially known cultivar *Hibiscus* 'Cranberry Crush', U.S. Plant Pat. No. 21,984. These plants are similar in most horticultural characteristics. However, plants of the new cultivar 'G21086' differ in the following:

1. 'G21086' has a cherry-red flower color, whereas comparison variety has a scarlet red flower color. Both the new variety and the comparison variety have large red eyes, however, the eye of the comparison variety is more distinct (sharply defined) where the eye color and the petal color meet.
2. 'G21086' has chocolate-brown to dark violet leaf color. This comparator has dark green leaves.
3. 'G21086' has a high number of shoots (5 to 8 or more) emerging from the base of the plant as it emerges from dormancy. This comparator typically has fewer shoots (3 to 5) as it emerges from dormancy.
4. 'G21086' emerges from dormancy about 4 weeks earlier than this comparator.
5. 'G21086' begins to flower about 3-4 weeks earlier than this comparator.
6. 'G21086' is compact and densely branched, forming a mounded plant 36" to 42" high and wide. This comparator is a taller plant, typically 48" to 60" high and wide.

'G21086' can also be compared to the commercially known cultivar *Hibiscus* 'PAS537702', unpatented. These cultivars are similar in most horticultural characteristics. However, plants of the new cultivar 'G21086' differ in the following:

1. 'G21086' has a cherry-red flower color, whereas this comparator has a light red flower color.
2. 'G21086' has chocolate brown to dark violet leaves, with slightly pubescent non-glossy leaf surfaces, above and below. This comparator has medium-green foliage with a dull, matte surface.
3. 'G21086' emerges up to a month earlier than this comparator when overwintered in-ground or in-container.
4. 'G21086' flowers up to two weeks earlier than this comparator when overwintered in-ground or in-container.
5. 'G21086' has a compact plant habit, 36" to 42" high and wide, and with dense basal branching. This comparator is more compact, about 24" to 30" high and wide.

BRIEF DESCRIPTION OF THE PHOTOGRAPHS

The accompanying photograph in FIG. 1 illustrates a 16-month old flowering plant in Summer (August).

Figure 2:
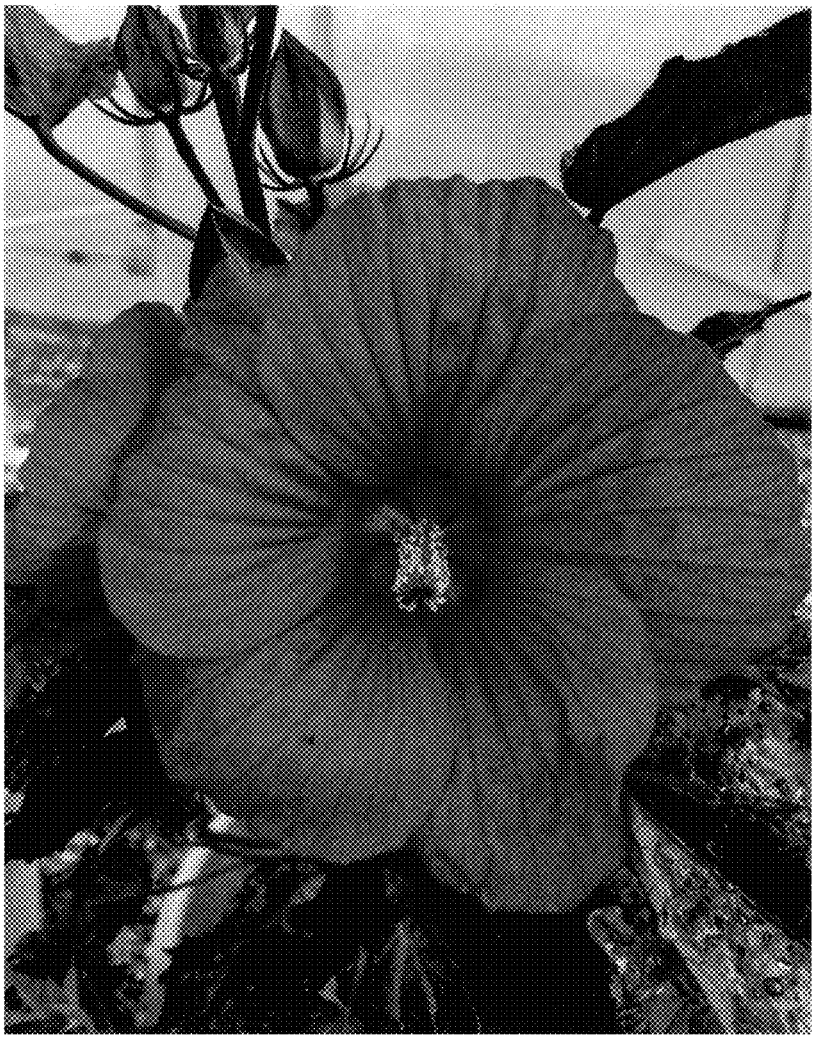

FIG. 2. is a close-up view of a typical flower of 'G21086'.

Figure 3:
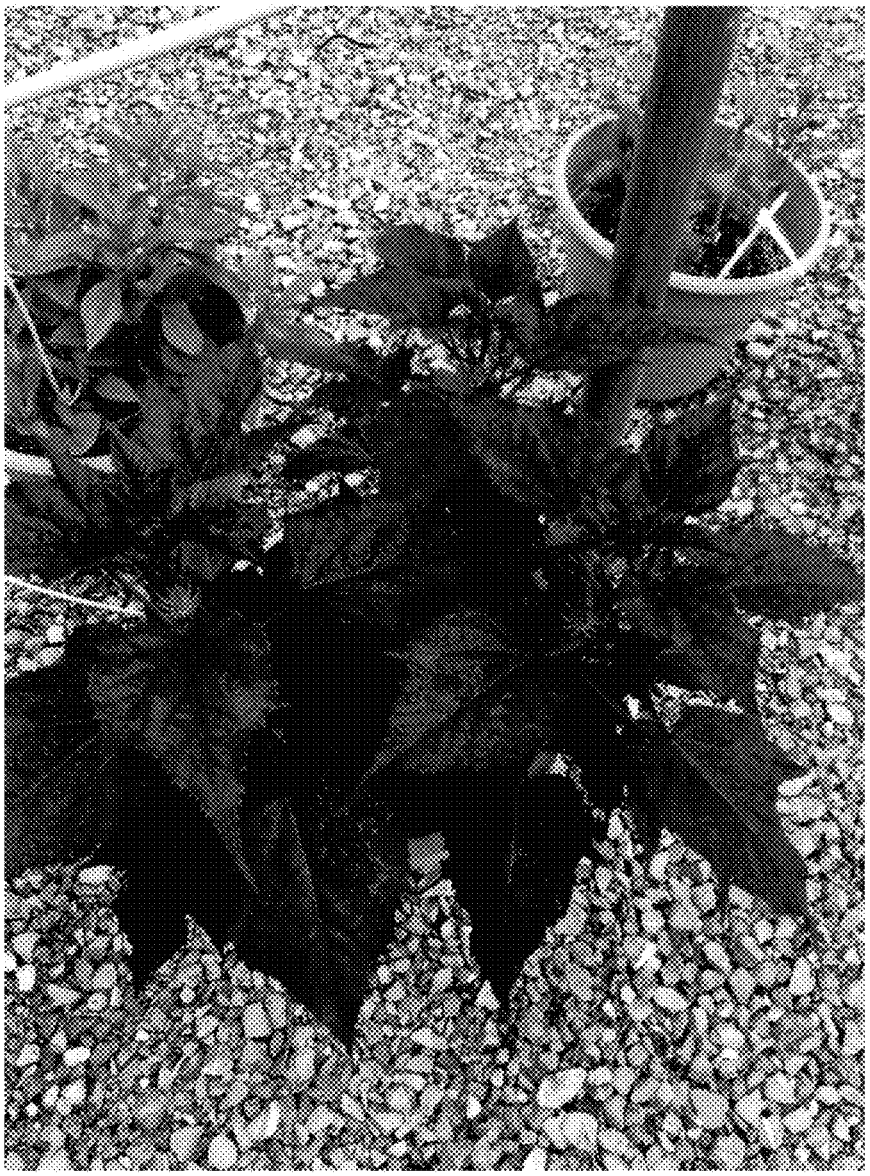

FIG. 3 is a photograph of a 14-month-old flowering plant in early Summer, showing the emerging foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2015, except where general terms of ordinary dictionary significance are used. The following observations and measurements describe 'G21086' plants grown outdoors from Spring to early Summer in Camarillo, California. The growing temperature ranged from about 7° C. to 30° C. during the day and from about 5° C. to 12° C. during the night. General light conditions are bright, normal sunlight. Measurements and numerical values represent averages of typical plant types. Plants are approximately 4 months old from a large rooted cutting. No chemical or photoperiodic treatments were given.

Botanical classification: *Hibiscus moscheutos* 'G21086'.

PROPAGATION

Root description: Woody, moderately well branched. Colored near Brown N200C, N200D and Grey 201B.

PLANT

Growth habit: Upright and somewhat outward. Moderately dense branching and foliage.
Height: Approximately 90 cm to 105 cm.
Plant spread: Approximately 90 cm to 105 cm.
Growth rate: Moderate.
Branching characteristics: Basal and lateral branching.
Length of branches: Approximately 35 to 70 cm.
Diameter branches: Approximately 7 to 10 mm.
Quantity of branches: Approximately 5 to 8 main basal branches.
Texture of lateral branches: Glabrous.
Color of lateral branches:
*Young*.—Near RHS Green 139A heavily or completely flushed Greyed-Purple 187A.
*Mature*.—Near RHS Green 137B.
Aspect: Approximately 30° to 60° angle from center of plant.
Strength of lateral branches: Very strong.
Internode length: Average range 3 to 6 cm.

FOLIAGE

Arrangement: Alternate.
Average length: Average range 5.5 to 9 cm.
Average width: Average range 4 to 6 cm.
Shape of blade: Somewhat founded deltate.
Apex: Acuminate.
Base: Rounded.
Attachment: Petiolate.
Margin: Moderately to densely serrate.
Texture of top surface: Sparsely pubescent.
Texture of bottom surface: Sparsely pubescent with protruding mid-vein.
Foliage color:
*Young foliage upper side*.—Near RHS Greyed-Purple 187B, 187C towards margins.

*Young foliage under side*.—Near RHS Greyed-Purple 185C.
*Mature foliage upper side*.—Near RHS Green 139A.
*Mature foliage under side*.—Near RHS Green 137C.

Venation:
*Type*.—Pinnate.
*Venation color upper side*.—Young foliage: Near RHS Red-Purple 58B flushed N57A. Mature foliage: Near Green 143C.
*Venation color under side*.—Young foliage: Near RHS Greyed-Purple 185C. Mature foliage: Near Green 143C.

Petiole:
*Length*.—Average range 3.8 to 7 cm.
*Diameter*.—Average 4 mm.
*Color*.—Young: Near RHS Red-Purple 58A flushed N57A, Mature: Near Green 137D.
*Texture*.—Finely pubescent.

INFLORESCENCE

Flower type and habit: Single, rotate, overlapping.
Flower longevity on plant: 2 to 3 days.
Persistence: Self-cleaning.
Fragrance: None.

Bud:
*Shape*.—Ovate.
*Length*.—3.5 cm.
*Diameter*.—2.2 cm at widest.
*Shape*.—Ovate.
*Texture*.—Scabrid.
*Color*.—RHS Yellow-Green 144C.

Flower size:
*Diameter*.—15 to 18 cm.
*Depth*.—8 cm.

Petals:
*Quantity*.—5.
*Arrangement*.—Rotate. Strongly overlapping.
*Length*.—6 to 9 cm.
*Width*.—6.8 to 8.2 cm at widest.
*Shape*.—Orbicular to obovate.
*Apex*.—Rounded.
*Base*.—Broad taper.
*Margin*.—Entire.
*Texture, upper and lower surfaces*.—Glabrous, slightly iridescent to shiny.
*Color*.—Eye — size and feathering: Eye is not strongly distinct from rest of petal. More of a flush of color. Extends less than 10% length of petal from petal base, minimal feathering. When opening, upper surface, main color: Near RHS Red 53B. When opening, upper surface, eye color: RHS Greyed-Purple N186A. When opening, lower surface: Near RHS Red 53B. Fully opened, upper surface, main color: Near RHS Red. Fully opened, upper surface, eye color: RHS Greyed-Purple N186A. Fully opened, lower surface: Near RHS Red 53B.

Calyx sepals:
*Quantity*.—5.
*Length*.—3.2 cm.
*Width*.—1.5 cm at widest part.
*Shape* (*overall*).—Deltate. Apex: Acute. Base: Truncate, fused.
*Margin*.—Entire.
*Color*.—Near RHS Green 137C.
*Texture*.—Lightly pubescent.

Epicalyx sepals:
*Quantity*.—5 to 7, typically 6.
*Length*.—2 cm.
*Width*.—6 mm at widest part.
*Shape* (*overall*).—Linear-lanceolate, fused at base.
*Apex*.—Acute.
*Base*.—Truncate.
*Margin*.—Entire.
*Color*.—RHS Green 137B flushed Greyed-Purple N186C.
*Texture*.—Lightly pubescent.

Peduncle:
*Length*.—Average range 4 to 6 cm.
*Diameter*.—5 mm.
*Angle*.—45° to the lateral branch.
*Strength*.—Moderately strong.
*Texture*.—Slightly pubescent.
*Color*.—RHS Green 137B flushed Greyed-Purple N186C.

REPRODUCTIVE ORGANS

Stamen stalk:
*Length*.—6.9 cm.
*Diameter*.—7 mm at base, tapering to 5 mm near apex.
*Color*.—Red 53A.
*Protruding beyond petals*.—Slightly protruding in fully opened flowers.

Stamens:
*Quantity*.—Typically between 40 and 50.

Anthers:
*Shape*.—Globular.
*Length*.—Approximately 2 mm.
*Color*.—RHS Yellow-Orange 16D.
*Pollen*.—Color: RHS Yellow-White 158D. Quantity: Sparse.

Pistil:
*Number*.—5.
*Length*.—9 mm.
*Style*.—Length: 5 mm. Color: Near RHS Red 53C.
*Stigma*.—Shape: Oblately globular. Color: RHS Red 53C. Ovary Color: RHS Green-White 157A.

OTHER CHARACTERISTICS

Disease resistance: Neither resistance nor susceptibility to diseases or pests normal to *Hibiscus* have been observed in this cultivar.
Drought tolerance and temperature tolerance: Hardy perennial, USDA zones 5-9.
Fruit/seed production: Not observed to date.

What is claimed is:

1. A new and distinct cultivar of *Hibiscus moscheutos* plant named 'G21086' as illustrated and described herein.

* * * * *